(12) United States Patent
Binder et al.

(10) Patent No.: US 8,969,614 B2
(45) Date of Patent: Mar. 3, 2015

(54) METHOD FOR PRODUCING COLOURLESS POLYISOCYANATES

(75) Inventors: Horst Binder, Lampertheim (DE); Matthias Kroner, Eisenberg (DE); Alexander Bayer, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 602 days.

(21) Appl. No.: 13/125,408

(22) PCT Filed: Oct. 19, 2009

(86) PCT No.: PCT/EP2009/063634
§ 371 (c)(1),
(2), (4) Date: Jun. 30, 2011

(87) PCT Pub. No.: WO2010/046327
PCT Pub. Date: Apr. 29, 2010

(65) Prior Publication Data
US 2011/0251423 A1    Oct. 13, 2011

(30) Foreign Application Priority Data

Oct. 22, 2008   (EP) .................................... 08167303

(51) Int. Cl.
| | | |
|---|---|---|
| C07C 251/00 | (2006.01) | |
| C08G 18/73 | (2006.01) | |
| C07C 263/18 | (2006.01) | |
| C07C 263/20 | (2006.01) | |
| C07D 251/34 | (2006.01) | |
| C08G 18/79 | (2006.01) | |
| C08G 18/75 | (2006.01) | |
| C08G 18/02 | (2006.01) | |
| C08G 18/18 | (2006.01) | |

(52) U.S. Cl.
CPC .............. C08G 18/73 (2013.01); C07C 263/18 (2013.01); C07C 263/20 (2013.01); C07D 251/34 (2013.01); C08G 18/792 (2013.01); C08G 18/798 (2013.01); C08G 18/755 (2013.01); C08G 18/022 (2013.01); C08G 18/1875 (2013.01)
USPC .......................................... 560/336; 560/330

(58) Field of Classification Search
None
See application file for complete search history.

(56) References Cited

U.S. PATENT DOCUMENTS

| | | | |
|---|---|---|---|
| 3,995,997 A | 12/1976 | Boehmke et al. | |
| 4,040,992 A | 8/1977 | Bechara et al. | |
| 4,324,879 A | 4/1982 | Bock et al. | |
| 4,335,212 A | 6/1982 | Wilson et al. | |
| 4,335,219 A | 6/1982 | Clarke et al. | |
| 4,454,317 A | 6/1984 | Disteldorf et al. | |
| 4,499,253 A | 2/1985 | Kerimis et al. | |
| 4,596,678 A | 6/1986 | Merger et al. | |
| 4,596,679 A | 6/1986 | Hellbach et al. | |
| 4,801,663 A | 1/1989 | Ueyanagi et al. | |
| 5,087,739 A | 2/1992 | Bohmholdt et al. | |
| 5,436,336 A | 7/1995 | Bruchmann et al. | |
| 5,919,887 A * | 7/1999 | Graf et al. ........................ 528/45 |
| 2011/0028579 A1 | 2/2011 | Zoellinger et al. | |

FOREIGN PATENT DOCUMENTS

| | | |
|---|---|---|
| DE | 26 31 733 | 2/1977 |
| DE | 28 06 731 | 8/1979 |
| DE | 29 01 479 | 7/1980 |
| DE | 38 06 276 | 9/1989 |
| DE | 100 13 186 | 9/2001 |
| DE | 100 13 187 | 10/2001 |
| DE | 10 2004 012571 | 9/2005 |
| DE | 10 2006 04346 | 4/2007 |
| DE | 10 2006 043464 | 4/2007 |
| DE | 102006043464 A1 | 4/2007 |
| EP | 0 010 589 | 5/1980 |
| EP | 0 126 299 | 11/1984 |
| EP | 0 126 300 | 11/1984 |
| EP | 0 330 966 | 9/1989 |
| EP | 0 355 443 | 2/1990 |
| EP | 0 355 479 | 2/1990 |
| EP | 0 377 177 | 7/1990 |
| EP | 0 569 804 | 11/1993 |
| EP | 0 630 928 | 12/1994 |
| EP | 0 668 271 | 8/1995 |
| EP | 0 798 299 | 10/1997 |
| EP | 0 896 009 | 2/1999 |
| EP | 1 668 271 | 1/2009 |
| JP | 03 036975 | 2/1991 |
| JP | 06041044 A  * | 2/1994 |
| WO | 97 45399 | 12/1997 |
| WO | 2005 087828 | 9/2005 |
| WO | 2008 068198 | 6/2008 |
| WO | WO 2009/121881 A1 | 10/2009 |

OTHER PUBLICATIONS

International Search Report issued Feb. 10, 2010 in PCT/EP09/063634 filed Oct. 19, 2009.

* cited by examiner

Primary Examiner — Sudhakar Katakam (74) Attorney, Agent, or Firm — Oblon, McClelland, Maier & Neustadt, L.L.P.

(57) ABSTRACT

The present invention relates to a process for preparing colorless polyisocyanates, in particular for reducing the color of polyisocyanates.

20 Claims, 4 Drawing Sheets

METHOD FOR PRODUCING COLOURLESS POLYISOCYANATES

The present invention relates to a process for preparing colorless polyisocyanates, in particular for reducing the color of polyisocyanates.

Various methods of reducing the color in polyisocyanates after they have been produced are known in the prior art.

JP 03036975 B discloses a process for decolorizing methylene-bridged polyphenylene polyisocyanates, in which the polyisocyanates are irradiated with light having a wavelength of from 200 to 700 nm, preferably from 300 to 500 nm.

Since the yellowing mechanism in aromatic isocyanates is attributable to a reaction of the aromatic amines with oxygen (the benzylic hydrogen atoms of the aromatic react with oxygen), the problem addressed by JP 03036975 B is different from that addressed by the present invention: in the present invention, the color number of firstly polyisocyanates and secondly aliphatic isocyanates is to be reduced, while in JP 03036975 B aromatic diisocyanates which have not been further treated by oligomerization of the isocyanate groups are treated. A person skilled in the art can therefore not assume that the teachings of JP 03036975 B can be applied to the problem to be solved here since the yellowing mechanism in aromatic isocyanates is naturally different from that in the case of aliphatic isocyanates since the latter do not have a benzylic group.

EP 377177 A1 describes the after-treatment of (cyclo)aliphatic polyisocyanates which have been prepared by trimerization of diisocyanates using the phosphines as catalyst with peroxide. The mixtures have to be thermally after-treated in this process.

WO 97/45399 describes improving the color of polyisocyanates which are based on hexamethylene diisocyanate and have been oligomerized using phosphines by means of peroxides.

DE 10 2006 043464 describes the treatment of a polyisocyanate with a peroxide or hydroperoxide.

EP 630928 A2 describes the improved color number and storage stability of polyisocyanates which have been prepared using ammonium salts or metal salts as catalyst which results from the addition of organic peracids. The acid function simultaneously serves to decompose the catalyst in order to stop the reaction.

The treatment of polyisocyanate with ozone or oxygen- or ozone-comprising gas mixtures is known from EP 569804.

These processes have the disadvantage that the added peroxide or hydroperoxide and the degradation products of the color-imparting components remain in the product.

It was an object of the present invention to develop a process by means of which a color which has already been formed in polyisocyanates can be removed without addition of substances foreign to the system.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

The object is achieved by a process for preparing colorless (cyclo)aliphatic polyisocyanates, in which the polyisocyanate which is based on (cyclo)aliphatic diisocyanates and has a higher than desired color number is irradiated with light having a wavelength of from 200 to 600 nm at an energy dose in this wavelength range which is sufficient to reduce the color number.

In addition, it has been found that the polyisocyanates which have been treated according to the invention have a lower viscosity than untreated polyisocyanates. This results in a smaller amount of solvent being sufficient to set the processing viscosity in the case of the polyisocyanates which have been treated according to the invention.

Suitable polyisocyanates for the process of the invention are, in particular, poly-isocyanates based on (cyclo)aliphatic diisocyanates.

In the present text, the term (cyclo)aliphatic is used as an abbreviation for cycloaliphatic or aliphatic.

Cycloaliphatic isocyanates are isocyanates which comprise at least one cycloaliphatic ring system.

Aliphatic isocyanates are isocyanates which comprise exclusively straight or branched chains, i.e. acyclic compounds.

The polyisocyanates which can be used according to the invention have no aromatic groups.

The monomeric isocyanates are preferably diisocyanates which bear exactly two isocyanate groups. However, they can in principle also be monoisocyanates having one isocyanate group, but these are less preferred.

It is in principle also possible to use higher isocyanates having an average of more than 2 isocyanate groups, but these are less preferred. Suitable isocyanates of this type are, for example, triisocyanates such as triisocyanatononane or 2'-isocyanatoethyl 2,6-diisocyanatohexanoate or mixtures of diisocyanates, triisocyanates and higher polyisocyanates.

The monomeric isocyanates comprise essentially no reaction products of the isocyanate groups with themselves.

The monomeric isocyanates are preferably isocyanates having from 4 to 20 carbon atoms. Examples of customary aliphatic diisocyanates are tetramethylene diisocyanate, pentamethylene 1,5-diisocyanate, hexamethylene diisocyanate (1,6-diisocyanatohexane), octamethylene diisocyanate, decamethylene diisocyanate, dodecamethylene diisocyanate, tetradecamethylene diisocyanate, derivatives of lysine diisocyanate (e.g. methyl or ethyl 2,6-diisocyanatohexanoate), trimethylhexane diisocyanate or tetramethylhexane diisocyanate. Examples of cycloaliphatic diisocyanates are 1,4-, 1,3- or 1,2-diisocyanatocyclohexane, 4,4'- or 2,4'-di(isocyanatocyclohexyl)methane, 1-isocyanato-3,3,5-trimethyl-5-(isocyanatomethyl)cyclohexane (isophorone diisocyanate), 1,3- or 1,4-bis(isocyanatomethyl)cyclohexane or 2,4- or 2,6-diisocyanato-1-methylcyclohexane and also 3 (or 4)-, 8 (or 9)-bis(isocyanatomethyl)tricyclo[5.2.1.0$^{2,6}$]decane isomer mixtures.

Particularly preferred diisocyanates are hexamethylene 1,6-diisocyanate, 1,3-bis(isocyanatomethyl)cyclohexane and isophorone diisocyanate; very particular preference is given to isophorone diisocyanate and hexamethylene 1,6-diisocyanate, in particular isophorone diisocyanate.

It is also possible for mixtures of isocyanates mentioned to be present.

Isophorone diisocyanate is usually present as a mixture of the cis and trans isomers, generally in a ratio of from about 60:40 to 80:20 (w/w), preferably in a ratio of from about 70:30 to 75:25 and particularly preferably in a ratio of about 75:25.

The content of isomeric compounds in the diisocyanate does not play a critical role for the process of the invention.

Thus, hexamethylene 1,6-diisocyanate can comprise, for example, a small proportion of 2- and/or 3-methylpentamethylene 1,5-diisocyanate.

For the purposes of the present invention, it is possible to use both polyisocyanates based on diisocyanates obtained by phosgenation of the corresponding amines and those based on diisocyanates prepared without use of phosgene, i.e. by phosgene-free processes. According to EP-A-0 126 299 (U.S. Pat. No. 4,596,678), EP-A-126 300 (U.S. Pat. No. 4,596,679) and EP-A-355 443 (U.S. Pat. No. 5,087,739), it is possible, for example, to prepare (cyclo)aliphatic diisocyanates such as hexamethylene 1,6-diisocyanate (HDI) by reaction of the (cyclo)aliphatic diamines with, for example, urea and alcohols to form (cyclo)aliphatic biscarbamic esters and thermal dissociation of these into the corresponding diisocyanates and alcohols. The synthesis is usually carried out continuously in a recirculation process and optionally in the presence of N-unsubstituted carbamic esters, dialkyl carbonates and other by-products recirculated from the reaction process. Diisocyanates obtained in this way generally have a very low or even unmeasurable proportion of chlorinated compounds, which can lead to advantageous color numbers of the products. It is a further advantage of the present invention that the process of the invention can be applied to aliphatic diisocyanates regardless of their method of preparation, i.e. regardless of whether they have been prepared via a phosgenation or a phosgene-free process.

In one embodiment of the present invention, the diisocyanate has a total content of hydrolyzable chlorine of less than 200 ppm, preferably less than 120 ppm, particularly preferably less than 80 ppm, very particularly preferably less than 50 ppm, in particular less than 15 ppm and especially less than 10 ppm. This can, for example, be measured by the ASTM method D4663-98. However, it is of course also possible to use diisocyanates having a higher chlorine content, for example up to 500 ppm.

It is of course also possible to use mixtures of diisocyanate which has been prepared by reaction of the corresponding diamine with, for example, urea and alcohols and dissociation of the resulting biscarbamic esters with a diisocyanate which has been obtained by phosgenation of the corresponding amine.

The polyisocyanates based on these diisocyanates are preferably the following compounds:
1) Polyisocyanates which are derived from aliphatic and/or cycloaliphatic diisocyanates and have isocyanurate groups. Particular preference is given here to the corresponding aliphatic and/or cycloaliphatic isocyanatoisocyanurates and in particular those based on hexamethylene diisocyanate and/or isophorone diisocyanate. The isocyanurates present are, in particular, trisisocyanatoalkyl or trisisocyanatocycloalkyl isocyanurates, which are cyclic trimers of the diisocyanates, or mixtures with their higher homologues having more than one isocyanurate ring. The isocyanatoisocyanurates generally have an NCO content of from 10 to 30% by weight, in particular from 15 to 25% by weight, and an average NCO functionality of from 2.6 to 8.
2) Polyisocyanates having aliphatically and/or cycloaliphatically bound preferably aliphatically and/or cycloaliphatically bound, and isocyanate groups and uretdione groups, in particular those derived from hexamethylene diisocyanate or isophorone diisocyanate. Uretdione diisocyanates are cyclic dimerization products of diisocyanates. The polyisocyanates having uretdione groups are, for the purposes of the present invention, obtained in admixture with other polyisocyanates, in particular those mentioned under 1). For this purpose, the diisocyanates can be reacted under reaction conditions under which both uretdione groups and the other polyisocyanates are formed, or the uretdione groups are formed first and these are subsequently converted into the other polyisocyanates or the diisocyanates are firstly converted into the other polyisocyanates and these are subsequently converted into products comprising uretdione groups.
3) Polyisocyanates having aliphatically or cycloaliphatically bound isocyanate groups and urethane and/or allophanate groups, as are obtained, for example, by reaction of an excess of diisocyanate, for example hexamethylene diisocyanate or isophorone diisocyanate, with monohydric or polyhydric alcohols. These polyisocyanates having urethane and/or allophanate groups generally have an NCO content of from 12 to 24% by weight and an average NCO functionality of from 2.1 to 4.5. Such polyisocyanates having urethane and/or allophanate groups can be prepared in the absence of catalysts or preferably in the presence of catalysts such as ammonium carboxylates or hydroxides, or allophanate formation catalysts, e.g. Zn(II) compounds, in each case in the presence of monohydric, dihydric or polyhydric, preferably monohydric, alcohols. The polyisocyanates having urethane and/or allophanate groups can also be prepared in admixture with other polyisocyanates, in particular those mentioned under 1).
4) Uretonimine-modified polyisocyanates.
5) Carbodiimide-modified polyisocyanates.
6) Hyperbranched polyisocyanates as are known, for example, from DE-A1 10013186 or DE-A1 10013187.
7) Polyurethane-polyisocyanate prepolymers derived from diisocyanates and/or polyisocyanates and alcohols.
8) Polyurea-polyisocyanate prepolymers.
9) Hydrophilically modified polyisocyanates, i.e. polyisocyanates which comprise, apart from the groups described under 1-10, groups which are formally formed by addition of molecules having NCO-reactive groups and hydrophilicizing groups onto the isocyanate groups of the above molecules. The hydrophilicizing groups are nonionic groups such as alkylpolyethylene oxide and/or ionic groups derived, for example, from phosphoric acid, phosphonic acid, sulfuric acid or sulfonic acid, or salts thereof.
10) Polyisocyanates comprising iminooxadiazinedione groups, preferably those derived from hexamethylene diisocyanate or isophorone diisocyanate. Such polyisocyanates comprising iminooxadiazinedione groups can be prepared from diisocyanates by means of specific catalysts.

In a preferred embodiment of the present invention, the polyisocyanate comprises at least one group selected from the group consisting of isocyanurates, urethanes and allophanates, preferably from the group consisting of isocyanurates and allophanates.

The polyisocyanate is particularly preferably a polyisocyanate comprising isocyanurate groups.

In a particularly preferred embodiment, the polyisocyanate is a polyisocyanate which is derived from hexamethylene 1,6-diisocyanate and/or isophorone diisocyanate and comprises isocyanurate groups, very particularly preferably a polyisocyanate which is based on isophorone diisocyanate and comprises isocyanurate groups.

In this text, the viscosity reported is the viscosity measured at 23° C. in accordance with DIN EN ISO 3219/A.3 in a cone-plate system at a shear rate of 250 s$^{-1}$, unless indicated otherwise.

The abovementioned polyisocyanates can also be present at least partly in blocked form.

The classes of compounds used for blocking are described, for example, in D. A. Wicks, Z. W. Wicks, Progress in Organic Coatings, 36, 148-172 (1999), 41, 1-83 (2001) and 43, 131-140 (2001).

Examples of classes of compounds used for blocking are phenols, imidazoles, triazoles, pyrazoles, oximes, N-hydroxyimides, hydroxybenzoic esters, secondary amines, lactams, CH-acidic cyclic ketones, malonic esters and alkyl acetoacetates.

The process of the invention can preferably be used for improving the color of polyisocyanates which have been obtained by reaction of monomeric isocyanates in the presence of at least one catalyst which has at least one quaternary nitrogen atom, particularly preferably in the presence of catalysts which have quaternary ammonium ions.

The ammonium ions are very particularly preferably those of the formula where $R^1$, $R^2$, $R^3$ and $R^4$ are each, independently of one another, optionally aryl-, alkyl-, aryloxy-, alkyloxy-, heteroatom- and/or heterocycle-substituted $C_1$—$C_{20}$-alkyl, $C_6$—$C_{12}$-aryl or $C_5$—$C_{12}$-cycloalkyl and $Y^-$ is any anion.

$R^1$, $R^2$, $R^3$ and $R^4$ in this formula are preferably selected independently of one another from the group consisting of methyl, ethyl, n-butyl, octyl, benzyl, 2-hydroxyethyl and 2-hydroxypropyl.

In a preferred embodiment, the anions $Y^-$ are selected from the group consisting of fluoride, hydroxide, carboxylate, carbonate and α-hydroxycarboxylate, particularly preferably selected from the group consisting of hydroxide, carboxylate, carbonate and α-hydroxycarboxylate and very particularly preferably selected from the group consisting of hydroxide and carboxylate.

The carboxylate ions are aromatic, aliphatic or cycloaliphatic, preferably aromatic or aliphatic and particularly preferably aliphatic, and have up to 12 carbon atoms, preferably from 1 to 8 carbon atoms.

Examples of particularly preferred carboxylate ions are formate, acetate, propionate and 2-ethylhexanoate, very particularly preferably formate and 2-ethylhexanoate, in particular 2-ethylhexanoate.

In further embodiments, the catalysts are of the following types:
quaternary ammonium carboxylates of the type described in U.S. Pat. Nos. 4,454,317 and 4,801,663;
quaternary ammonium phenoxides having a zwitterionic structure of the type described in U.S. Pat. No. 4,335,219;
ammonium phosphonates and phosphates of the type described in U.S. Pat. No. 4,499,253;
mixtures of alkali metal fluorides and quaternary ammonium or phosphonium salts as described in EP-A 355479; EP 798299 B1 or EP 896009 B1 for preparing mixtures of isocyanurate with asymmetric isocyanurates, iminooxodiazinedione,
ammonium α-hydroxycarboxylates as described in WO 2005/087828,
ammonium carbonates or ammonium betaines as described in EP 668271,
quaternary hydroxyalkylammonium compounds of the formula as catalyst according to DE-A-26 31 733 (U.S. Pat. No. 4,040,992).

Here, the radicals $R^5$ to $R^9$ are each, independently of one another, hydrogen, $C_1$—$C_4$-alkyl or benzyl and $R^9$ may also be $C_5$—$C_8$-alkyl.

Particularly useful catalysts for the process are quaternary ammonium salts corresponding to the formula where $Y^\ominus$=carboxylate ($R^{14}COO^-$), fluoride ($F^-$), carbonate ($R^{14}O(CO)O^-$) or hydroxide ($OH-$), as are described for $Y^-=OH^-$ in U.S. Pat. No. 4,324,879 and in DE-A-2,806,731 and DE-A-2,901,479.

The radical $Y^\ominus$ is preferably a carboxylate, carbonate or hydroxide, particularly preferably a carboxylate or hydroxide and very particularly preferably a carboxylate.

$R^{14}$ here is hydrogen, $C_1$—$C_{20}$-alkyl, $C_6$-$C_{12}$-aryl or $C_7$-$C_{20}$-arylalkyl, each of which may optionally be substituted.

$R^{14}$ is preferably hydrogen or $C_1$-$C_8$-alkyl.

If a catalyst having a hydroxide ion as anion is used, the reaction is preferably carried out at a reduced content of carbon dioxide ($CO_2$), for example of less than 20 ppm, preferably less than 10 ppm and particularly preferably less than 5 ppm, as described in EP 330966 A2.

Preferred quaternary ammonium salts are those in which the radicals $R^{10}$ to $R^{13}$ are identical or different alkyl groups which have from 1 to 20, preferably from 1 to 4, carbon atoms and may optionally be substituted by hydroxyl or phenyl groups.

Two of the radicals $R^{10}$ to $R^{13}$ together with the nitrogen atom and optionally a further nitrogen or oxygen atom can also form a heterocyclic, five-, six- or seven-membered ring. The radicals $R^{10}$ to $R^{12}$ can in each case also be ethylene radicals which together with the quaternary nitrogen atom and a further tertiary nitrogen atom form a bicyclic triethylenediamine structure, provided that the radical $R^{13}$ is then a hydroxyalkyl group which has from 2 to 4 carbon atoms and in which the hydroxyl group is preferably in the 2 position relative to the quaternary nitrogen atom. The hydroxyl-substituted radical or hydroxyl-substituted radicals can also comprise other substituents, for example $C_1$-$C_4$-alkyloxy substituents.

The ammonium ions can also be part of a monocyclic or polycyclic ring system, for example a ring system derived from piperazine, morpholine, piperidine, pyrrolidine, quinuclidine or diazabicyclo[2.2.2]octane.

Examples of groups $R^{10}$ to $R^{13}$ having from 1 to 20 carbon atoms are, independently of one another, methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, hetadecyl, octadecyl, 1,1-dimethylpropyl, 1,1-dimethylbutyl, 1,1,3,3-tetramethylbutyl, benzyl, 1-phenylethyl, 2-phenylethyl, α,α-dimethylbenzyl, benzhydryl, p-tolylmethyl, 1-(p-butylphenyl)ethyl, p-chlorobenzyl, 2,4-dichlorobenzyl, p-methoxybenzyl, m-ethoxy-benzyl, 2-cyanoethyl, 2-cyanopropyl, 2-methoxycarbonethyl, 2-ethoxycarbonylethyl, 2-butoxycarbonylpropyl, 1,2-di(methoxycarbonyl)ethyl, 2-methoxyethyl, 2-ethoxyethyl, 2-butoxyethyl, diethoxymethyl, diethoxyethyl, chloromethyl, 2-chloroethyl, trichloromethyl, trifluoromethyl, 1,1-dimethyl-2-chloroethyl, 2-methoxyisopropyl, 2-ethoxyethyl, 2-hydroxyethyl, 2-hydroxypropyl, 3-hydroxypropyl, 4-hydroxybutyl, 6-hydroxyhexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl, 6-ethoxyhexyl, phenyl, tolyl, xylyl, α-naphthyl, β-naphthyl, 4-diphenylyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, methoxyphenyl, dimethoxyphenyl, methylnaphthyl, isopropylnaphthyl, chloronaphthyl, 2,6-dimethylphenyl, 2,4,6-trimethylphenyl, 2,6-dimethoxyphenyl, 2,6-dichlorophenyl, cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, chlorocyclohexyl, dichlorocyclohexyl, dichlorocyclopentyl, norbornyl or norbornenyl.

The radicals $R^{10}$ to $R^{13}$ are preferably each $C_1$-$C_4$-alkyl. $R^{13}$ can also be benzyl or a radical of the formula where $R^{15}$ and $R^{16}$ can each be, independently of one another, hydrogen or $C_1$-$C_4$-alkyl.

Particularly preferred radicals $R^{10}$ to $R^{13}$ are, independently of one another, methyl, ethyl and n-butyl and $R^{13}$ can also be benzyl, 2-hydroxyethyl and 2-hydroxypropyl.

Preference is given to using the following catalysts for the process of the invention:

Quaternary ammonium hydroxides, preferably N,N,N-trimethyl-N-benzylammonium hydroxide and N,N,N-trimethyl-N-(2-hydroxypropyl)ammonium hydroxide, as described in DE-A-38 06 276, with the proviso that the process is then preferably carried out under a reduced content of carbon dioxide.

Hydroxyalkyl-substituted quaternary ammonium hydroxides as described in EP-A-10 589 (US-A-4 324 879).

In the present text, optionally aryl-, alkyl-, aryloxy-, alkyloxy-, heteroatom- and/or heterocycle-substituted $C_1$-$C_{20}$-alkyl is, for example, methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, hetadecyl, octadecyl, eicosyl, 1,1-dimethylpropyl, 1,1-dimethylbutyl, 1,1,3,3-tetramethylbutyl, benzyl, 1-phenylethyl, 2-phenylethyl, α,α-dimethylbenzyl, benzhydryl, p-tolylmethyl, 1-(p-butylphenyl)ethyl, p-chlorobenzyl, 2,4-dichlorobenzyl, p-methoxybenzyl, methoxybenzyl, 2-cyanoethyl, 2-cyanopropyl, 2-methoxycarbonethyl, 2-ethoxycarbonylethyl, 2-butoxycarbonylpropyl, 1,2-di(methoxycarbonyl)ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, 2-chloroethyl, trichloromethyl, trifluoromethyl, 1,1-dimethyl-2-chloroethyl, 2-methoxyisopropyl, 2-ethoxyethyl, butylthiomethyl, 2-dodecylthioethyl, 2-phenylthioethyl, 2,2,2-trifluoroethyl, 2-hydroxyethyl, 2-hydroxypropyl, 3-hydroxypropyl, 4-hydroxybutyl, 6-hydroxyhexyl, 2-aminoethyl, 2-aminopropyl, 3-aminopropyl, 4-aminobutyl, 6-aminohexyl, 2-methylaminoethyl, 2-methylaminopropyl, 3-methylaminopropyl, 4-methylaminobutyl, 6-methylaminohexyl, 2-dimethylaminoethyl, 2-dimethylaminopropyl, 3-dimethylaminopropyl, 4-dimethylaminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl, optionally aryl-, alkyl-, aryloxy-, alkyloxy-, heteroatom- and/or heterocycle-substituted $C_5$-$C_{12}$-aryl is, for example, phenyl, tolyl, xylyl, α-naphthyl, β-naphthyl, 4-diphenylyl, chlorophenyl, dichlorophenyl, trichlorophenyl, difluorophenyl, methylphenyl, dimethylphenyl, trimethylphenyl, ethylphenyl, diethylphenyl, iso-propylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl or ethoxymethylphenyl, optionally aryl-, alkyl-, aryloxy-, alkyloxy-, heteroatom- and/or heterocycle- substituted $C_5$-$C_{12}$-cycloalkyl is, for example, cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl or a saturated or unsaturated bicyclic system such as norbornyl or norbornenyl, divalent $C_2$-$C_9$-alkylene radicals which can also be constituents of an arylene or cycloalkylene radical are, for example, 1,2-ethylene, 1,2-propylene, 1,3-propylene, 1,6-hexylene, 2,2,4-trimethylhexylene, 1,4-cyclohexylene, isopropylidene-1,4-dicyclohexylene, 1,2- 1,3- or 1,4-phenylene, 4,4'-biphenylene, 4,4'-bisphenylmethylene, 1,3-, 1,4- or 1,5-naphthylene, 3,3'-dimethyl-4,4'-diphenylene, 3,3'-dichloro-4,4'-diphenylene, 2,4- or 2,6-pyridyl, 1,4-anthraquinonediyl, m- or p-toluylene, 4,6-dimethyl-1,3-phenylene, 4,6-dichloro-1,3-phenylene, 5-chloro-1,3-phenylene, 5-hydroxy-1,3-phenylene, 5-methoxy-1,3-phenylene, 2,3-dimethyl-1,4-phenylene, m- or p-xylylene, methylenedi-p-phenylene, isopropylidenedi-p-phenylene, thiodi-p-phenylene, dithiodi-p-phenylene, sulfodi-p-phenylene, carbonyldi-p-phenylene and $C_1$-$C_4$-alkyl is, for example, methyl, ethyl, propyl, isopropyl, n-butyl, sec-butyl or tert-butyl, preferably methyl, ethyl or n-butyl, particularly preferably methyl or ethyl and very particularly preferably methyl.

These quaternary ammonium catalysts are prepared in a known manner, for example by reacting a tertiary amine with an alkylene oxide in an aqueous-alcoholic medium (cf. U.S. Pat. No. 3,995,997, column 2, lines 19-44).

Examples of suitable tertiary amines are trimethylamine, tributylamine, 2-dimethylaminoethanol, triethanolamine, dodecyldimethylamine, N,N-dimethylcyclohexylamine, N-methylpyrrolidine, N-methylmorpholine and 1,4-diazabicyclo[2.2.2]octane. Examples of suitable alkylene oxides are ethylene oxide, propylene oxide, 1,2-butylene oxide, styrene oxide and methoxypropylene, ethoxypropylene or phenoxypropylene oxide.

The most preferred catalysts are N-(2-hydroxypropyl)-N,N,N-trimethylammonium 2-ethylhexanoate (DABCO TMR®) and N-(2-hydroxypropyl)-N,N,N-trimethylammonium 2-formate (DABCO TMR®-2) from Air Products.

Preference is also given to trimerization catalysts as are known from DE 10 2004 012571 A1, there in particular paragraphs [0017] to [0027], and from EP-A1 668 271, there in particular from page 4, line 16 to page 6, line 47, which are hereby incorporated by reference into the present disclosure.

The catalysts are generally used in amounts of up to 1000 ppm by weight, preferably from about 5 to 500 ppm by weight, particularly preferably from 10 to 100 ppm by weight, based on the isocyanate used.

The catalysts can be used in pure form or in solution. The catalyst can be dissolved in a suitable solvent to aid handling. Suitable solvents for this purpose are, for example, alcohols, diols, ketones, ethers and esters. The solvents mentioned in this text which are inert toward isocyanate groups are suitable as solvent, depending on the type of catalyst. Dimethylformamide or dimethyl sulfoxide can likewise be used as solvent for the catalysts.

According to the invention, the preparation of the polyisocyanates is not subject to any restrictions. For example, it can be carried out as follows:

a) the monomeric isocyanate is firstly reacted in the presence of a catalyst.

Step a) can be carried out batchwise or continuously and can, in a typical embodiment, be carried out, for example, as follows:

In step a), the reaction of the reactants takes place in at least one reaction zone. The average total residence time in step a) can be up to 7 hours, preferably up to 90 minutes, particularly preferably up to 60 minutes, very particularly preferably up to 30 minutes and in particular up to 20 minutes.

The average total residence time in step a) is generally at least 2 minutes, preferably at least 5 minutes, particularly preferably at least 10 minutes, very particularly preferably at least 15 minutes and in particular at least 20 minutes.

The reaction zone can be backmixed or exhibit plug flow; combinations thereof are also conceivable.

The reaction zones can be, for example, a series of a plurality of stirred vessels (cascade of stirred vessels) or at least one stirred vessel which is divided into a plurality of zones by appropriate division of the reaction volume, for example by means of dividing plates (cascaded stirred vessel) or combinations thereof.

The temperature in a backmixed reactor system is generally in the range from 40° C. to 170° C., preferably from 45° C. to 160° C., particularly preferably in the range from 50 to 150° C. and very particularly preferably in the range from 55 to 140° C.

The catalysts are generally used in amounts of up to 1000 ppm by weight, preferably from about 5 to 500 ppm by weight, particularly preferably from 10 to 100 ppm by weight, based on the isocyanate used.

b) When the desired conversion has been reached in step a), at least one compound which is able to deactivate the catalyst in step a) is added to the reaction mixture.

The conversion can be chosen differently as a function of the isocyanate used. In general, a conversion of from 5 to 60% (based on the NCO content before the reaction) is sought, preferably from 5 to 35%.

To stop the reaction in step b), the deactivating agent is used in a molar ratio of, for example, from 0.5 to 20, particularly preferably from 0.6 to 3, very particularly preferably from 0.8 to 2, based on the amount of catalyst used.

Suitable deactivating agents are in principle inorganic salts, e.g. hydrogen chloride, phosphorous acid or phosphoric acid, carboxylic acid halides, e.g. acetyl chloride or benzoyl chloride, sulfonic acids or sulfonic esters, e.g. methanesulfonic acid, p-toluenesulfonic acid, methyl or ethyl p-toluenesulfonate, m-chloroperbenzoic acid and preferably dialkyl phosphates such as di-2-ethylhexyl phosphate and dibutyl phosphate.

The use of carbamate compounds as described in WO 2008/068198 is also conceivable.

The addition of the stopping agent is generally carried out at the reaction temperature, but can also be carried out at higher or lower temperatures, for example up to 30° C. lower, preferably up to 20° C. lower and particularly preferably up to 10° C. lower.

As an alternative, the reaction mixture from step a) can also be stopped, or stopping can be completed, by thermally deactivating the catalyst. Catalysts which have β-hydroxyalkyl groups bound to ammonium groups are suitable for this purpose. In this case, the temperature is briefly increased to at least 100° C., preferably at least 110° C. and particularly preferably at least 120° C., preferably by passage through a distillation apparatus, as described in step c).

c) Removal of the unreacted isocyanate (D) from the reaction mixture obtained in this way.

The polyisocyanate-comprising reaction mixture prepared in this way is subsequently freed of any solvents or diluents present and/or preferably of excess, unreacted isocyanates in a manner known per se in a step c), for example by thin film distillation at a temperature of from 90 to 220° C., optionally under reduced pressure, optionally with additional passage of inert stripping gas through the apparatus, so that the polyisocyanates having isocyanurate groups can be obtained with a content of monomeric isocyanates of, for example, less than 1.0% by weight, preferably less than 0.5% by weight, particularly preferably less than 0.3% by weight, very particularly preferably less than 0.2% by weight and in particular not more than 0.1% by weight.

Apparatuses used for this purpose are flash evaporators, falling film evaporators, thin film evaporators and/or short path evaporators, which can optionally be superposed by a short column.

The distillation is generally carried out at a pressure in the range from 0.1 to 300 hPa, preferably below 200 hPa and particularly preferably below 100 hPa.

In a preferred embodiment, the distillation is carried out in a plurality of stages, for example from 2 to 5 stages, preferably from 2 to 4 stages and particularly preferably 3 or 4 stages.

In this case, the pressure is advantageously reduced from stage to stage, for example from an initial 300-500 hPa via 100-300 hPa to 10-100 hPa and subsequently to 0.1-10 hPa.

The temperature in the individual distillation stages is in each case in the range from 90 to 220° C.

The first stage is advantageously carried out in a simple apparatus, for example a circulation, flash or cylinder evaporator, and the subsequent stages are carried out in more complicated apparatuses, for example in falling film evaporators, thin film evaporators, for example Sambay® or Luwa evaporators, or short path evaporators. It is advantageous to employ designs of the apparatuses which reduce the residence time of the streams and thus the thermal stress to which they are subjected, for example by emission of intermediate vessels or reservoirs, short paths through tubes or the smallest possible volumes of the bottom regions for the liquid phase.

The distillate separated off, which comprises monomeric isocyanate, is preferably recirculated to step a) and, supplemented by fresh isocyanate, reused in the reaction.

In the process of the invention, the polyisocyanate is irradiated with light having a wavelength of from 200 to 600 nm, preferably from 210 to 500 nm, particularly preferably from 220 to 450 nm and very particularly preferably from 220 to 420 nm.

The radiation source used should preferably have at least one emission maximum in this wavelength range.

The energy dose is in principle not subject to an upper limit. It is sufficient when the desired color numbers are reached.

The energy dose should be sufficient to reduce the color number by at least 1 Hazen, preferably by at least 2 Hazen, particularly preferably by at least 3 Hazen, very particularly preferably by at least 5 Hazen and in particular by at least 10 Hazen. It can be desirable to reduce the color number by at least 15 Hazen or even by at least 20 Hazen.

Radiation doses of 20-40 000 J/cm$^2$ can usually be employed. Higher doses can be useful, for example, if the product is strongly colored.

Suitable radiation sources are, for example, low-pressure mercury vapor lamps, intermediate-pressure mercury vapor lamps and high-pressure lamps which may optionally be undoped or gallium- or iron-doped and also fluorescent tubes, impulse lamps, metal halide lamps, excimer lamps, lasers, LEDs, pulsed lamps (electronic flash) or halogen lamps.

It is of course also possible to use a plurality of identical or different radiation sources in order to achieve the desired energy dose or spectral distribution. These can also radiate in different wavelength ranges in each case.

It is also possible to filter out specific wavelength ranges from the irradiation spectrum by means of suitable optical filters in order to avoid undesirable photoreactions.

It is likewise possible to choose the glass between radiation source and product to be irradiated so that undesirable light wavelengths of the radiation source are absorbed. For example, the relatively expensive fused silica can, depending on the radiation source, be replaced by borosilicate glass in order to filter out short-wavelength radiation which damages the product.

It is possible to use optical filters which, for example, block out very short-wavelength radiation, preferably below 250 nm, or filters which, for example, block out both short-wavelength UV radiation and long-wavelength IR radiation (=heat radiation), in particular of the wavelengths from 780 nm to 1 mm.

The polyisocyanate can, according to the invention, be irradiated for a time of from 5 minutes to 600 hours, preferably from 20 minutes to 8 hours.

The temperature of the polyisocyanate during irradiation plays only a minor role. The lower temperature limit is set by the desirability of the polyisocyanate remaining pumpable, while the upper limit is set by its thermal stability. The temperature is preferably from ambient temperature to 130° C., particularly preferably from 20° C. to 100° C., very particularly preferably from 30° C. to 80° C. and in particular from 30° C. to 70° C.

Irradiation can, according to the invention, be carried out continuously or batchwise. Here, the polyisocyanate can be at rest or preferably be kept in motion, for example by pump circulation or stirring.

In a preferred embodiment, the radiation source or a plurality thereof, if desired or required, is/are dipped into a reservoir, for example a storage tank, comprising polyisocyanate and the polyisocyanate is set into motion.

In a further preferred embodiment, the radiation source or a plurality of radiation sources, if desired or required, is/are positioned in a reservoir, for example a storage tank, in or above the polyisocyanate and the polyisocyanate is set into motion.

In a further preferred embodiment, the polyisocyanate is passed through a tube which is at least partially transparent to the desired wavelength of the irradiating light, for example a tube made of fused silica, and the polyisocyanate is irradiated. Arrangements for such apparatuses are known in principle from mains water treatment and can in the case of chemical plants be matched to requirements in a typical manner.

It is also conceivable for irradiation to be carried out in an apparatus during the preparation, for example in the removal of unreacted monomeric isocyanate (see above), by, for example, providing a falling film evaporator with a fused silica window or placing a radiation source inside the falling film evaporator.

To reduce the viscosity, it can be necessary to admix the polyisocyanate with a solvent.

Examples of such solvents are aromatic and/or (cyclo) aliphatic hydrocarbons and mixtures thereof, halogenated hydrocarbons, ketones, esters and ethers.

Preference is given to aromatic hydrocarbons, (cyclo)aliphatic hydrocarbons, alkyl alkanoates, alkoxylated alkyl alkanoates and mixtures thereof.

Particular preference is given to monoalkylated or polyalkylated benzenes and naphthalenes, alkyl alkanoates and alkoxylated alkyl alkanoates and also mixtures thereof.

As aromatic hydrocarbon mixtures, preference is given to those which comprise predominantly aromatic $C_7$-$C_{14}$-hydrocarbons and can have a boiling range of from 110 to 300° C., with particular preference being given to toluene, o-, m- or p-xylene, trimethylbenzene isomers, tetramethylbenzene isomers, ethylbenzene, cumene, tetrahydronaphthalene and mixtures comprising these.

Examples of such hydrocarbon mixtures are the Solvesso® grades from ExxonMobil Chemical, in particular Solvesso® 100 (CAS No. 64742-95-6, predominantly $C_9$- and $C_{10}$-aromatics, boiling range about 154-0 178° C.), Solvesso® 150 (boiling range about 182-207° C.) and Solvesso® 200 (CAS No. 64742-94-5), and also the Shellsol® grades from Shell, Caromax® (e.g. Caromax® 18) from Petrochem Carless and Hydrosol from DHC (e.g. as Hydrosol® A 170). Hydrocarbon mixtures of paraffins, cycloparaffins and aromatics are also commercially available under the names Kristallöl (for example Kristallöl 30, boiling range about 158-198° C. or Kristallöl 60: CAS No. 64742-82-1), white spirit (for example likewise CAS No. 64742-82-1) or Solvent naphtha (light: boiling range about 155-180° C., heavy: boiling range about 225-300° C.). The aromatics content of such hydrocarbon mixtures is generally greater than 90% by weight, preferably more than 95% by weight, particularly preferably more than 98% by weight and very particularly preferably more than 99% by weight. It can also be advantageous to use hydrocarbon mixtures having a particularly reduced content of naphthalene.

The content of aliphatic hydrocarbons is generally less than 5% by weight, preferably less than 2.5% by weight and particularly preferably less than 1% by weight.

Halogenated hydrocarbons are, for example, chlorobenzene and dichlorobenzene or isomer mixtures thereof and also para-chlorobenzotrifluoride (Oxsol® 100).

Esters are, for example, n-butyl acetate, ethyl acetate, 1-methoxyprop-2-yl acetate and 2-methoxyethyl acetate.

Ethers are, for example, THF, dioxane and the dimethyl, diethyl or di-n-butyl ethers of ethylene glycol, diethylene glycol, triethylene glycol, propylene glycol, dipropylene glycol or tripropylene glycol.

(Cyclo)aliphatic hydrocarbons are, for example, decalin, alkylated decalin and isomer mixtures of linear or branched alkanes and/or cycloalkanes, for example petroleum ether or ligroin.

Preference is also given to n-butyl acetate, ethyl acetate, 1-methoxyprop-2-yl acetate, 2-methoxyethyl acetate, tert-butyl acetate and their mixtures, in particular with the above-mentioned aromatic hydrocarbon mixtures.

Preference is also given to ketones, for example acetone, methyl ethyl ketone and methyl amyl ketone.

Such mixtures can be produced in a volume ratio of from 5:1 to 1:5, preferably in a volume ratio of from 4:1 to 1:4, particularly preferably in a volume ratio of from 3:1 to 1:3 and very particularly preferably in a volume ratio of from 2:1 to 1:2.

Preferred examples are butyl acetate/xylene, methoxypropyl acetate/xylene 1:1, butyl acetate/solvent naphtha 100 1:1, butyl acetate/Solvesso® 100 1:2 and Kristallöl 30/Shellsol® A 3:1.

Polyisocyanates which have a color can be decolorized again by means of the process of the invention and subsequently also have good color stability during storage. As a result, the polyisocyanates which have been treated in this way have good suitability for use in surface coatings:

The polyisocyanates obtained according to the invention can be used for producing polyurethanes and polyurethane coatings, for example for one-component, two-component, radiation-curable or powder coating systems and surface coatings prepared thereby, which can be used for coating various substrates such as wood, wood veneer, paper, paperboard, cardboard, textile, leather, nonwovens, plastic surfaces, glass, ceramic, mineral building materials, metals or coated metals.

When used in coating compositions, the polyisocyanates according to the invention can be employed, in particular, in primers, fillers, pigmented topcoats, undercoats, clear coatings and topcoats in the field of automobile repair coating or large vehicle coating.

Such coating compositions are particularly suitable for applications in which particularly high application safety, exterior weathering resistance, visual appearance and resistance to solvents, chemicals and water are required, as in automobile repair coating and large vehicle coating and also for commercial vehicles in the agricultural and building sectors.

Such coating compositions are suitable as or in exterior coatings, i.e. applications which are exposed to daylight, preferably on parts of buildings, interior coatings, coatings on (large) vehicles and aircraft and industrial applications, bridges, buildings, power pylons, tanks, containers, pipelines, power stations, chemical plants, ships, cranes, piles, sheet piling, valves, pipes, fittings, flanges, couplings, halls, roofs and building steel. In particular, the coating compositions according to the invention are used as or in clear coatings and topcoats in the automobile sector. Further preferred fields of use are can coating and coil coating.

They are particularly suitable as primers, fillers, pigmented topcoats and clear coatings in the field of industrial coatings, wood coatings, automobile coatings, in particular OEM coatings, or decorative coatings. The coating compositions are very particularly suitable for applications in which a particularly high application safety, exterior weathering resistance, visual appearance, scratch resistance and resistance to solvents and/or chemicals are required. Due to their low color number and high color stability, they are of particular interest for coating compositions for clear coatings. They are of particular interest in combination with antioxidants and Lewis-acid compounds, optionally in the presence of solvents, in particular during storage.

EXAMPLES

The color number measurement in the present text is, unless indicated otherwise, reported in Hazen (Hz) in accordance with DIN EN 1557 measured on a Lico 300 instrument from Lange in a 5 cm measurement cell having a volume of 5 ml.

Example 1

600 g of isophorone diisocyanate (IPDI) prepared by a phosgene process were placed in a reaction vessel at room temperature, maintained under reduced pressure for 1 hour and subsequently heated to 50° C.

160 ppm of N,N,N-trimethyl-N-benzylammonium hydroxide was added in the form of a 3% strength solution in ethylhexanol. The temperature rose from 50° C. to 61° C. The mixture was subsequently heated to 65° C. The NCO value reached 32.2% after an after-reaction time of 100 minutes.

The reaction was stopped by rapid heating to 140° C. After filtration, the excess IPDI was virtually completely removed in a thin film evaporator at a heating medium temperature of 195° C. The product was dissolved in butyl acetate to produce a 70% strength solution. A yellowish product solution (color number 68 Hz) having an NCO content of 12.4% is obtained.

Example 2

The procedure of example 1 was repeated, but the reaction was stopped by means of a molar amount of butyl carbamate, based on the catalyst used, at 65° C. after an NCO value of 32% had been reached.

Color number: 39 Hz

Example 3

The procedure of example 1 was repeated, but DABCO® TMR was used as trimerization catalyst. The reaction was stopped by means of a molar amount of XHC-20 (2-hydroxyethyl carbamate, from Huntsman), based on the catalyst used, at 65° C. after an NCO value of 32.1% had been reached.

Color number: 35 Hz

Example 4

The experiment of example 3 was repeated using IPDI prepared by means of a urea process.

Color number: 42 Hz

Example 5

The experiment of example 3 was repeated using IPDI from a urea process. However, the reaction was stopped thermally at 140° C.

Color number: 55 Hz

Example 6

The experiment of example 4 was repeated using IPDI from a phosgene process. The reaction was stopped thermally at 140° C. at an NCO value of 32.5%.

Color number: 88 Hz

Example 7

600 g of fresh distilled IPDI from a phosgene process were admixed with 6 g of methanol and stirred at 90° C. for 2 hours. The temperature was then reduced to 65° C. 150 ppm of DABCO® TMR were then added. At an NCO value of 31.7%, an equimolar amount of butyl carbamate, based on the catalyst used, was added.

The mixture was subsequently worked up by distillation at 190° C./1 mbar.

Color number: 41 Hz

Example 8

600 g of fresh distilled IPDI from a urea process were admixed with 6 g of ethanol and stirred at 90° C. for 2 hours. The temperature was then reduced to 65° C. 160 ppm of DABCO® TMR were then added. At an NCO value of 31.7%, an equimolar amount of XHC-20 (from Huntsman), based on the catalyst used, was added. Further processing was carried out in a manner analogous to that described for example 1.
Color number: 35 Hz

Example 9

600 g of a mixture of 50% of IPDI from a phosgene process and 50% from a urea process were admixed with 8 g of 2-ethylhexanol and stirred at 115° C. for 2 hours. The temperature was then reduced to 65° C. 185 ppm of DABCO® TMR dissolved in 2-ethyl-1,3-hexanediol (2% strength solution) were then added. At an NCO value of 31.7%, a two-fold equimolar amount of tert-butyl carbamate based on the catalyst used, was added. Further processing was carried out in a manner analogous to that described for example 1. Color number: 37 Hz Example 10 600 g of a mixture of 50% of IPDI from a phosgene process and 50% from a urea process were admixed with 8 g of 2-ethylhexanol and stirred at 115° C. for 2 hours. The temperature was then reduced to 65° C. 185 ppm of DABCO® TMR dissolved in 2-ethyl-1,3-hexanediol (2% strength solution) were then added. At an NCO value of 32.7%, the reaction was stopped thermally at 140° C. Further processing was carried out in a manner analogous to that described for example 1.
Color number: 85 Hz

Example 11

588 g of hexamethylene 1,6-diisocyanate (HDI) from a phosgene process were placed in a reaction vessel at room temperature, maintained under nitrogen for 1 hour and subsequently heated to 40° C. 60 ppm of N,N,N-trimethyl-N-benzylammonium hydroxide were added in the form of a 3% strength solution in ethylhexanol.

The temperature rose from 40° C. to 52° C. The mixture was subsequently heated to 60° C. The NCO value reached 40.6% after an after-reaction time of 100 minutes. The reaction was stopped by rapid heating to 130° C. After filtration, the excess HDI was virtually completely removed in a thin film evaporator at an external temperature of 170° C.

A yellowish product (color number 78 Hz) having an NCO content of 21.7% and a viscosity of 2400 mPas is obtained.

Example 12

The procedure of example 1 was repeated but DABCO® TMR was used as trimerization catalyst. The reaction was stopped by means of a molar amount of XHC-20 (from Huntsman), based on the catalyst used, at 65° C. after an NCO value of 40.6% had been reached.

Color number after distillation: 65 Hz

Example 13

588 g of fresh distilled HDI from a urea process were admixed with 12 g of methanol and stirred at 80° C. for 2 hours. The temperature was then reduced to 65° C. 150 ppm of DABCO® TMR were then added. At an NCO value of 38.7%, an equimolar amount of butyl carbamate, based on the catalyst used, was added.

The mixture was stirred for another 1 hour and the NCO value was measured again.

NCO value after the after-reaction: 38.6%

The mixture was subsequently worked up by distillation at 170° C./1 mbar.

Color number after distillation: 48 Hz

Example 14

588 g of freshly distilled HDI from a phosgene process were admixed with 12 g of ethyl hexanol and stirred at 115° C. for 2 hours. The temperature was then reduced to 65° C. 24 ppm of N,N,N-trimethyl-N-benzylammonium hydroxide dissolved in 2-ethyl-1,3-hexanediol (0.5% strength solution) were then added. At an NCO value of 38.7%, a two-fold equimolar amount of tert-butyl carbamate, based on the catalyst used, was added.

The mixture was stirred for another 1 hour and the NCO value was measured again. NCO value after the after-reaction: 38.7% Further processing was carried out as described under example 7.

Color number after distillation: 58 Hz

Example 15

588 g of freshly distilled HDI mixture from the phosgene process and urea process (1:1) were admixed with 12 g of ethylhexanol and stirred at 115° C. for 2 hours. The temperature was then reduced to 65° C. 24 ppm of DABCO® TMR dissolved in 2-ethyl-1,3-hexanediol (0.5% strength solution) were then added. At an NCO value of 38.7%, an equimolar amount of tert-butyl carbamate, based on the catalyst used, was added. The mixture was stirred for another 1 hour and the NCO value was measured again.

NCO value after the after-reaction: 38.7%

Further processing was carried out as described under example 7.

Color number after distillation: 51 Hz

Results After Irradiation

The various samples were irradiated with the following UV lamps for 4 hours in a Panacol-Elosol irradiation apparatus:

| Type of lamp | Energy [mW/cm2] |
| --- | --- |
| ES 450 | 17.2 |
| ES 460 | 5.6 |
| ES 465 | 14.1 |
| ES 470 | 8.6 |

A UV meter (sensor No. 724 (UV-A range)) from Hönle was used as energy measuring instrument.

Figure 1:
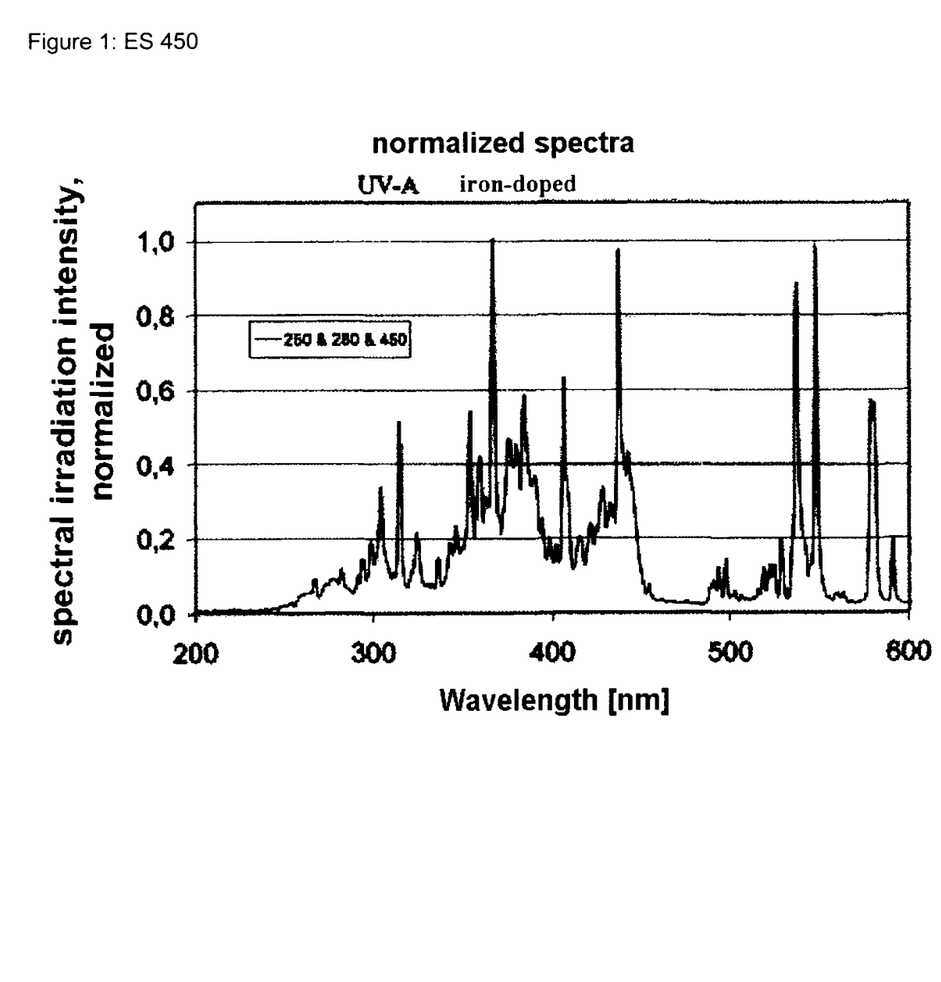
FIG. 1 provides a normalized spectra for ES450.
Figure 2:
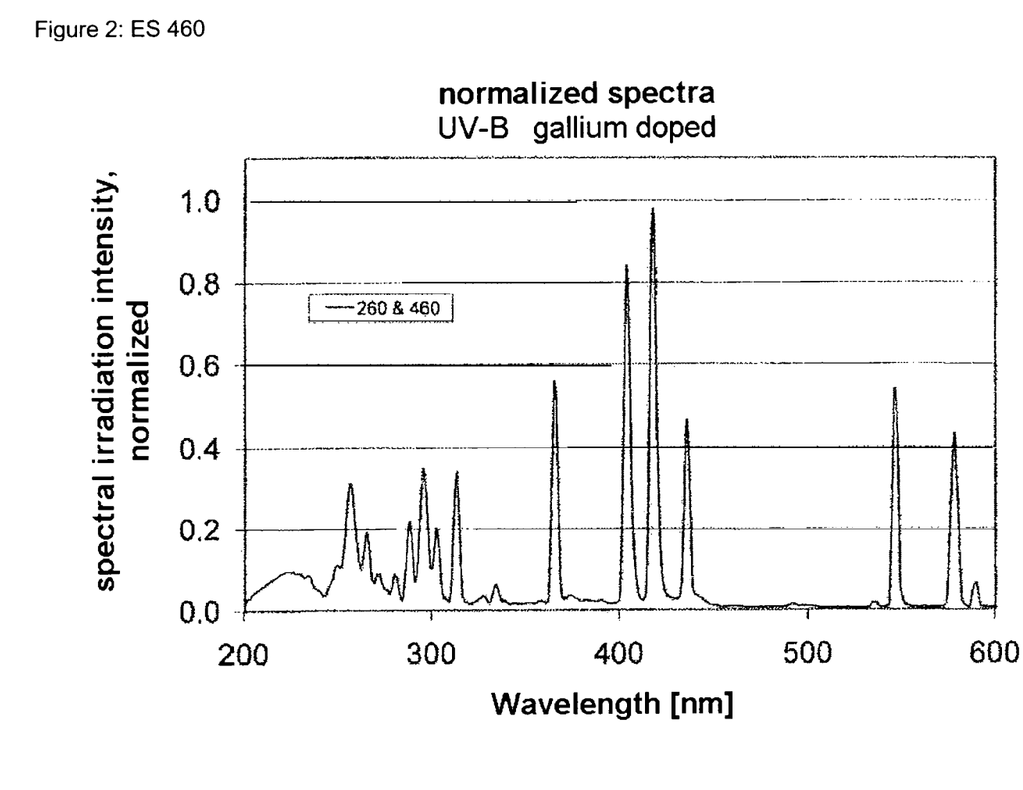
FIG. 2 provides a normalized spectra for ES460.
Figure 3:
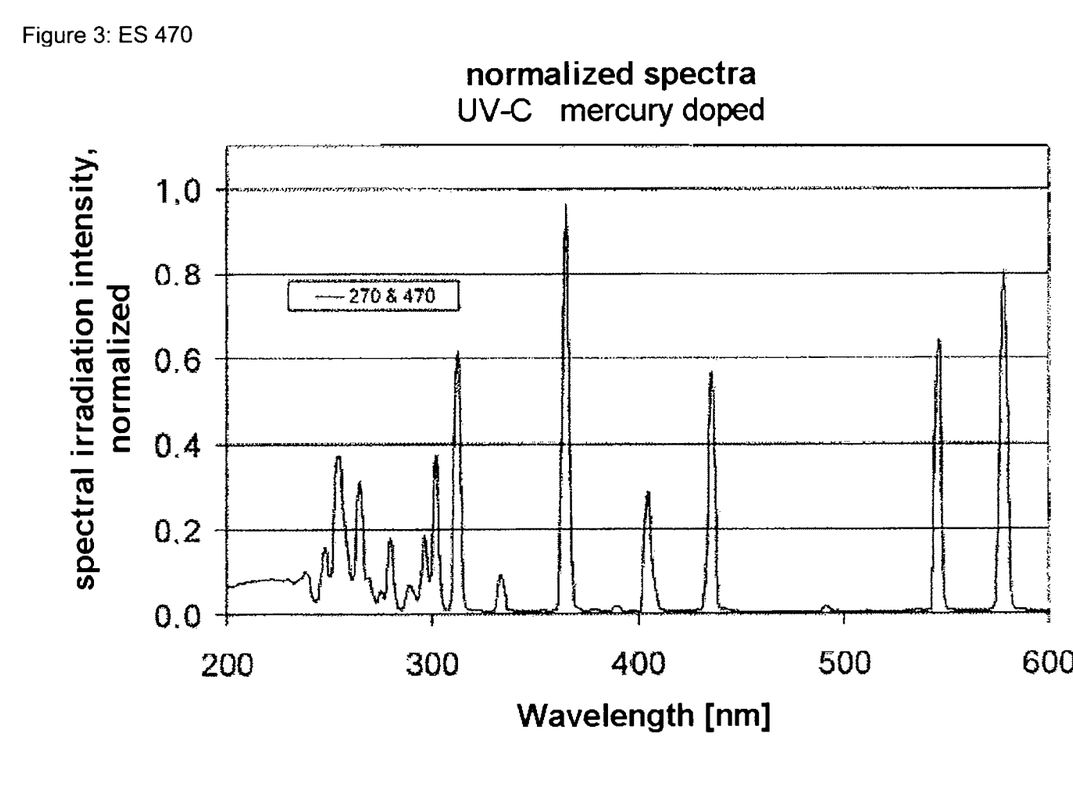
FIG. 3 provides a normalized spectra for ES470.
Figure 4:
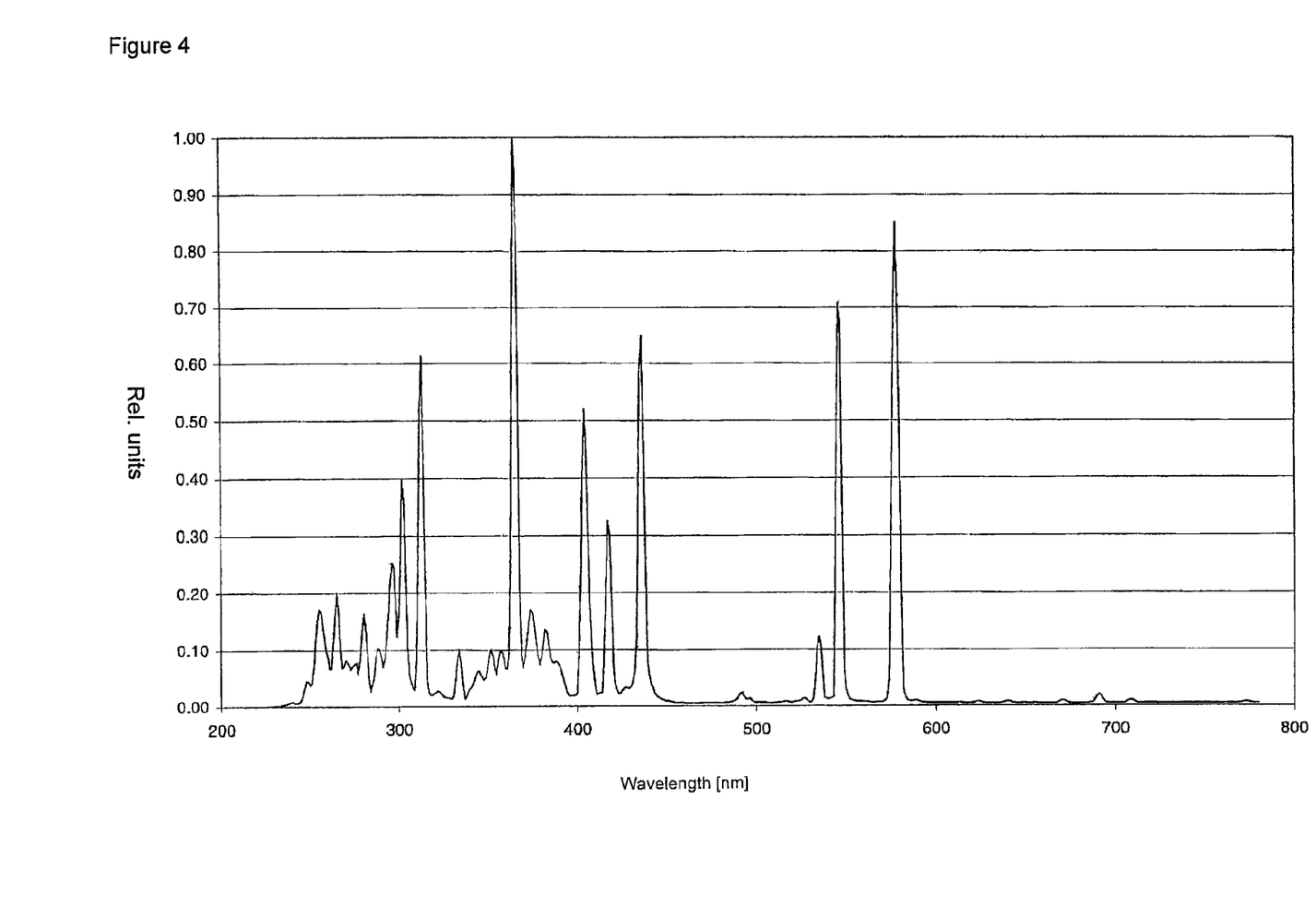
FIG. 4 provides a normalized spectra for ES465.

The spectra of the lamps are shown in FIGS. 1 to 4:
FIG. 1: ES 450
FIG. 2: ES 460
FIG. 3: ES 470
FIG. 4: ES 465
The examples are shown in table 1.

TABLE 1

| Example | Color number [Hz] before irradiation | Color number [Hz] after irradiation ES 450 | ES 460 | ES 465 | ES 470 |
|---|---|---|---|---|---|
| 1 | 68 | 27 | 32 | 35 | 37 |
| 2 | 39 | 19 | 21 | 24 | 21 |
| 3 | 35 | 21 | 24 | 23 | 25 |
| 4 | 42 | 25 | 26 | 27 | 26 |
| 5 | 55 | 31 | 32 | 35 | 32 |
| 6 | 88 | 34 | 45 | 38 | 46 |
| 7 | 41 | 23 | 26 | 24 | 27 |
| 8 | 35 | 20 | 28 | 24 | 31 |
| 9 | 37 | 21 | 29 | 24 | 29 |
| 10 | 85 | 31 | 42 | 34 | 45 |
| 11 | 78 | 23 | 36 | 31 | 38 |
| 12 | 65 | 25 | 32 | 26 | 32 |
| 13 | 48 | 31 | 35 | 32 | 35 |
| 14 | 58 | 32 | 35 | 33 | 37 |
| 15 | 51 | 29 | 33 | 30 | 35 |

It can be seen that all types of lamp were able to reduce the product color.

The samples were stored for 9 weeks (we) at 50° C. after the UV treatment.

The examples are shown in table 2.

TABLE 2

| | | ES 450 | | | | | | | ES 470 | |
|---|---|---|---|---|---|---|---|---|---|---|
| | unirradiated | 0 | 9 | ES 460 | | ES 465 | | 0 | 9 |
| Example | 0 we | 9 we | we | we | 0 we | 9 we | 0 we | 9 we | we | we |
| 1 | 68 | 135 | 27 | 33 | 32 | 35 | 35 | 34 | 37 | 65 |
| 2 | 39 | 82 | 19 | 25 | 21 | 28 | 24 | 26 | 21 | 45 |
| 3 | 35 | 79 | 21 | 26 | 24 | 31 | 23 | 29 | 25 | 35 |
| 4 | 42 | 92 | 25 | 31 | 26 | 35 | 27 | 31 | 26 | 47 |
| 5 | 55 | 105 | 31 | 37 | 32 | 39 | 35 | 38 | 32 | 54 |
| 6 | 88 | 145 | 34 | 41 | 45 | 44 | 38 | 49 | 46 | 52 |
| 7 | 41 | 79 | 23 | 31 | 26 | 36 | 24 | 35 | 27 | 54 |
| 8 | 35 | 67 | 20 | 27 | 28 | 31 | 24 | 32 | 31 | 42 |
| 9 | 37 | 69 | 21 | 33 | 29 | 41 | 24 | 33 | 29 | 37 |
| 10 | 85 | 134 | 31 | 41 | 42 | 42 | 34 | 51 | 45 | 58 |
| 11 | 78 | 156 | 23 | 31 | 36 | 45 | 31 | 47 | 38 | 42 |
| 12 | 65 | 132 | 25 | 35 | 32 | 48 | 26 | 41 | 32 | 53 |
| 13 | 48 | 98 | 31 | 55 | 35 | 62 | 32 | 47 | 35 | 61 |
| 14 | 58 | 78 | 32 | 43 | 35 | 49 | 33 | 41 | 37 | 57 |
| 15 | 51 | 68 | 29 | 41 | 33 | 51 | 30 | 39 | 35 | 43 |

A significantly improved storage stability of the product properties was observed for all samples.

Example 16

To test the storage stability further, the polyisocyanates produced were tested in a formulation comprising the polyisocyanate, a Lewis-acid catalyst and organic solvents at elevated temperature.

For this test, 50% by weight of polyisocyanate were mixed with 50% by weight of solvent comprising 75% of solvent naphtha and 25% of butyl acetate comprising 1000 ppm by weight of dibutyltin dilaurate (based on the total amount of solvent). After mixing the formulation at room temperature, the mixture was stored at 50° C. under a nitrogen atmosphere.

The color increase was measured after 1, 2, 4 and 8 weeks.

| Sample | Irradiation with ES 450 | Color after formulation | Storage at 50° C. | | | |
|---|---|---|---|---|---|---|
| | | | 1 week | 2 weeks | 4 weeks | 8 weeks |
| 1 | no | 45 | 71 | 118 | 165 | 298 |
| | yes | 16 | 19 | 65 | 112 | 240 |
| 2 | no | 33 | 51 | 88 | 112 | 240 |
| | yes | 15 | 18 | 34 | 97 | 211 |
| 4 | no | 32 | 46 | 81 | 123 | 231 |
| | yes | 16 | 18 | 38 | 102 | 179 |
| 5 | no | 41 | 63 | 112 | 157 | 289 |
| | yes | 25 | 27 | 67 | 109 | 245 |
| 7 | no | 29 | 41 | 82 | 110 | 213 |
| | yes | 14 | 17 | 34 | 94 | 167 |
| 8 | no | 27 | 37 | 75 | 93 | 191 |
| | yes | 12 | 15 | 46 | 78 | 154 |
| 10 | no | 61 | 93 | 165 | 245 | 398 |
| | yes | 23 | 31 | 113 | 187 | 365 |
| 11 | no | 58 | 89 | 161 | 231 | 393 |
| | yes | 18 | 20 | 113 | 189 | 312 |
| 12 | no | 51 | 81 | 141 | 197 | 347 |
| | yes | 21 | 24 | 87 | 150 | 310 |
| 13 | no | 37 | 57 | 111 | 160 | 261 |
| | yes | 22 | 29 | 79 | 140 | 235 |

Example 17

The viscosity of the samples produced as described in example 16 was also measured by means of a Physica Rheolab MC1 in accordance with DIN 5301 and a shear rate of $250\ s^{-1}$.

| Sample | Irradiation | Viscosity after formulation | Storage at 50° C. | | | |
|---|---|---|---|---|---|---|
| | | | 1 week | 2 weeks | 4 weeks | 8 weeks |
| 1 | no | 970 | 1110 | 1271 | 1631 | 1940 |
| | yes | 972 | 995 | 1170 | 1506 | 1754 |
| 2 | no | 1130 | 1305 | 1561 | 2046 | 2260 |
| | yes | 1170 | 1300 | 1527 | 1964 | 2146 |
| 4 | no | 1030 | 1170 | 1372 | 1844 | 2060 |
| | yes | 1035 | 1179 | 1419 | 1761 | 2016 |
| 5 | no | 1231 | 1510 | 1760 | 2296 | 2610 |
| | yes | 1250 | 1441 | 1701 | 2213 | 2310 |
| 7 | no | 960 | 1109 | 1270 | 1651 | 2140 |
| | yes | 965 | 1090 | 1283 | 1630 | 1930 |
| 8 | no | 920 | 1070 | 1231 | 1631 | 1951 |
| | yes | 923 | 1051 | 1206 | 1551 | 1753 |
| 10 | no | 1031 | 1189 | 1381 | 1849 | 2317 |
| | yes | 1040 | 1156 | 1302 | 1691 | 2080 |
| 11 | no | 530 | 613 | 701 | 917 | 1121 |
| | yes | 542 | 612 | 695 | 879 | 1084 |
| 12 | no | 578 | 661 | 806 | 1067 | 1239 |
| | yes | 602 | 625 | 751 | 974 | 1204 |
| 13 | no | 510 | 597 | 732 | 953 | 1160 |
| | yes | 519 | 586 | 681 | 889 | 1038 |

It can be seen that the UV-irradiated samples achieved better results in respect of both the color values and the viscosities.

The invention claimed is:
1. A process for reducing a color number of a polyisocyanate comprising a (cyclo)aliphatic polyisocyanate, the process comprising:
   irradiating a polyisocyanate, which comprises at least one (cyclo)aliphatic diisocyanate,
   with light having a wavelength in a range of from 200 to 600 nm, wherein the process is carried out without addition of a ozone, oxygen, an ozone comprising gas, a peroxide or a hydroperoxide.

2. The process of claim 1, wherein said polyisocyanate comprises, in reacted form, at least one compound selected from the group consisting of isophorone diisocyanate and hexamethylene 1,6-diisocyanate.

3. The process of claim 1, wherein the polyisocyanate comprises at least one moiety selected from the group consisting of an isocyanurate group, a urethane group, and an allophanate group.

4. The process of claim 1, wherein said polyisocyanate is obtained by reaction of at least one monomeric isocyanate in the presence of at least one catalyst having at least one quaternary nitrogen atom.

5. The process of claim 4, wherein the catalyst is a compound of formula (I)

wherein $R^1$, $R^2$, $R^3$, and $R^4$ are each, independently of one another, are $C_1$-$C_{20}$-alkyl, $C_6$-$C_{12}$-aryl, or $C_5$-$C_{12}$-cycloalkyl, each of which is optionally substituted with an aryl group, alkyl group, aryloxy group, heteroatom, or heterocycle, and $Y^-$ is any anion.

6. The process of claim 5, wherein $R^1$, $R^2$, $R^3$, and $R^4$ are independently selected from the group consisting of methyl, ethyl, n-butyl, octyl, benzyl, 2-hydroxyethyl, and 2-hydroxypropyl.

7. The process of claim 5, wherein the anion $Y^-$ is selected from the group consisting of fluoride, hydroxide, carboxylate, carbonate, and α-hydroxycarboxylate.

8. The process of claim 5, wherein the anion $Y^-$ is selected from the group consisting of formate, acetate, propionate, and 2-ethylhexanoate.

9. The process of claim 2, wherein the polyisocyanate comprises at least one moiety selected from the group consisting of an isocyanurate group, a urethane group, and an allophanate group.

10. The process of claim 2, wherein said polyisocyanate is obtained by reaction of at least one monomeric isocyanate in the presence of at least one catalyst having at least one quaternary nitrogen atom.

11. The process of claim 3, wherein said polyisocyanate is obtained by reaction of at least one monomeric isocyanate in the presence of at least one catalyst having at least one quaternary nitrogen atom.

12. The process of claim 1, wherein said color number is reduced by at least 1 Hazen.

13. The process of claim 1, wherein said color number is reduced by at least 2 Hazen.

14. The process of claim 1, wherein said color number is reduced by at least 3 Hazen.

15. The process of claim 1, wherein said color number is reduced by at least 5 Hazen.

16. The process of claim 1, wherein irradiation is with a radiation dose of 20-40,000 J/cm².

17. The process of claim 1, wherein irradiation is for a time of from 5 minutes to 600 h.

18. The process of claim 1, wherein irradiation is for a time of from 20 minutes to 8 h.

19. The process of claim 1, wherein said light has a wavelength of from 210 to 500 nm.

20. The process of claim 1, wherein said light has a wavelength of from 220 to 420 nm.

* * * * *